United States Patent [19]

Haruki et al.

[11] 4,044,593
[45] Aug. 30, 1977

[54] CHROMATOGRAPH

[75] Inventors: Tatsuro Haruki; Yoshiro Hayashi, both of Kyoto, Japan

[73] Assignee: Shimadzu Seisakusho Ltd., Kyoto, Japan

[21] Appl. No.: 442,055

[22] Filed: Feb. 13, 1974

Related U.S. Application Data

[63] Continuation of Ser. No. 201,646, Nov. 24, 1971, abandoned.

[30] Foreign Application Priority Data

Mar. 31, 1971 Japan .............................. 46-23282[U]
Mar. 31, 1971 Japan .............................. 46-23283[U]

[51] Int. Cl.² ............................................ G01N 31/08
[52] U.S. Cl. .................................................. 73/23.1
[58] Field of Search ................ 73/23.1, 422 GC, 431; 55/67, 197, 386; 23/232 R, 232 C, 254 R; 219/520, 521, 523, 536

[56] References Cited

U.S. PATENT DOCUMENTS

| | | | |
|---|---|---|---|
| 3,062,037 | 11/1962 | Donner et al. | 73/23.1 |
| 3,062,038 | 11/1962 | Ayers | 73/23.1 |
| 3,097,518 | 7/1963 | Taylor et al. | 73/23.1 |
| 3,152,470 | 10/1964 | Reinecke et al. | 73/23.1 |
| 3,199,274 | 8/1965 | Norem et al. | 73/23.1 X |
| 3,229,501 | 1/1966 | Henze et al. | 73/23.1 X |
| 3,298,788 | 1/1967 | Dewar et al. | 73/23.1 X |
| 3,309,504 | 3/1967 | Rosso et a'. | 73/23.1 |
| 3,385,099 | 5/1968 | Diem et al. | 73/23.1 |
| 3,403,545 | 10/1968 | Carter | 73/23.1 |
| 3,690,838 | 9/1972 | Luckey | 23/232 R X |
| 3,751,629 | 8/1973 | Eisler | 219/521 X |

OTHER PUBLICATIONS

Beckman Gas Chromatograph, Beckman Instruments Inc., Nov. 1965 p. 3.

*Primary Examiner*—Richard C. Queisser
*Assistant Examiner*—Stephen A. Kreitman
*Attorney, Agent, or Firm*—Fidelman, Wolffe & Waldron

[57] ABSTRACT

A chromatograph having removable modular analysis units fitting into a chamber within the chromatograph housing, each unit including a column, sample introduction portion and detector. Each modular unit includes a block of thermally conductive material which encloses substantial portions of the sample introduction means and detector and is provided with an exposed surface adapted to contact heating means contained in the chromatograph housing.

9 Claims, 8 Drawing Figures

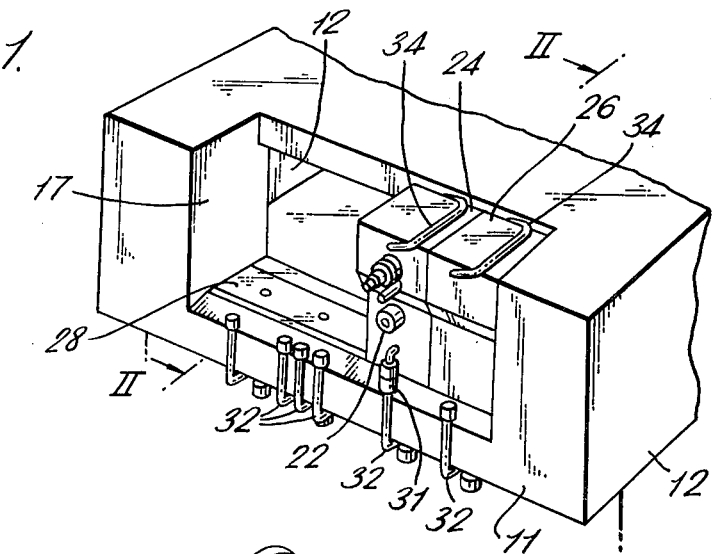
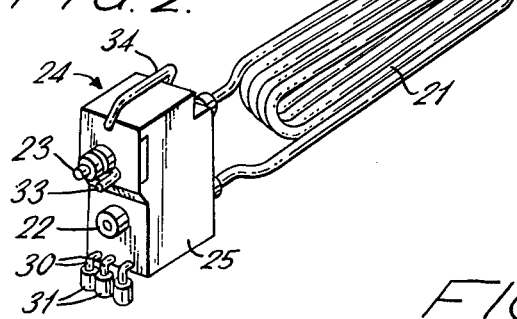
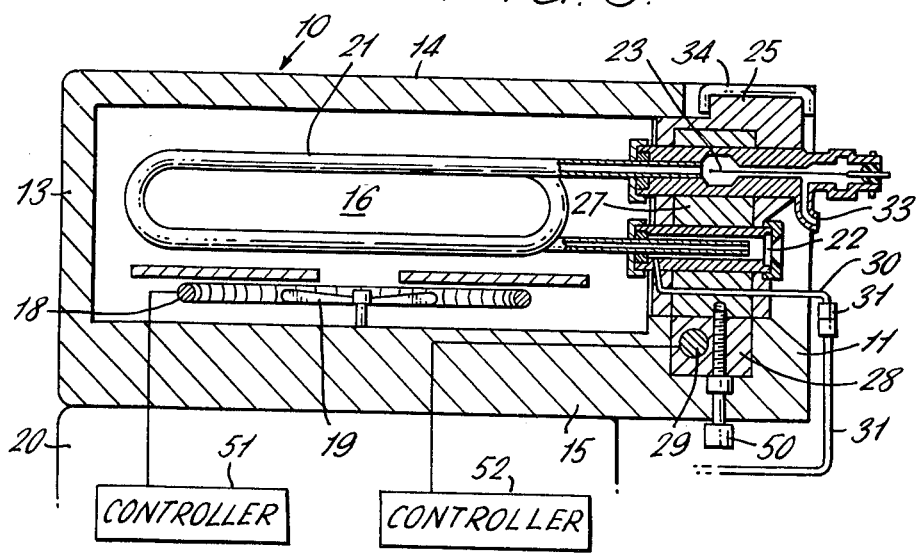

CHROMATOGRAPH

This is a continuation of application Ser. No. 201,646, filed Nov. 24, 1971, now abandoned.

This invention relates to a chromatograph and more particularly to improvements in the construction of that portion of a chromatograph which includes a column, a sample introducing portion and a detector.

Generally speaking, a chromatograph comprises a principal portion and a subsidiary portion. The former chiefly comprises a column, a column chamber for keeping the column at a required temperature, a detector and a detector chamber for keeping the detector at a required temperature, while the latter chiefly comprises controllers for the temperature of the column chamber and the detector chamber, an amplifier for the output of the detector, an indicator and/or recorder, a controller for the flow rate of carrier fluid, etc. This invention is particularly concerned with the construction of the principal portion of the chromatograph.

When conducting chromatographic analyses, it sometimes is required that the column, the sample introducing portion, and the detector used for a sample previously analyzed should be replaced by new and clean ones for analysis of a different sample, since any trace of the constituents of the previous sample remaining in these portions of the apparatus would detrimentally affect accurate analysis of the next sample. Removal of the these elements is also necessary for cleaning or repair purposes. In the prior art chromatographs known to the present inventors it is a time-consuming job to remove these elements from the apparatus for repair or replacement.

In some cases it is required to have various samples analyzed in rapid succession. It would be unpractical from the economic point of view to provide as many chromatographs as there are different samples to be analyzed.

Accordingly, the primary object of the invention is to provide a new and improved chromatograph which is provided with at least one separable analysis unit or module which comprises a combination of a columm, a sample introducing portion and a detector.

Another object of the invention is to provide such a chromatograph as aforesaid, wherein said analysis unit is attached to the column chamber of the apparatus so that the unit can be quickly and easily removed therefrom.

Another object of the invention is to provide such a chromatograph as aforesaid, wherein there are provided a plurality of analysis units which can selectively attached to, and removed from, the apparatus independently of the others so that many different samples can be analyzed in rapid succession.

Another object of the invention is to provide such a chromatograph as aforesaid, wherein it is easily possible to remove the column from lthe apparatus for cleaning, repair or replacement.

Another object of the invention is to provide such a chromatograph as aforesaid, wherein the temperature of the detector and the sample introducing portion can easily be controlled independently of the temperature control of the column chamber.

Another object of the invention is to provide such a chromatograph as aforesaid, wherein access can be made to the outer ends of the sample introducing portion and the detector and also to the inlet and outlet pipes of the carrier gas from one and the same side of the housing so that operation associated with these elements can be easily and quickly conducted.

Still another object of the invention is to provide such a chromatograph as aforesaid, which is compact in size and occupies a smaller site for installation than the prior art apparatus.

The invention with its above and other objects, features and advantages will become apparent from the following detailed description of some preferred embodiments of the invention with reference to the accompanying drawing, wherein the same reference numerals in different figures denote corresponding parts, and wherein:

FIG. 1 is a perspective view of one embodiment of the invention, with some of the analysis units being taken out from the housing;

FIG. 2 is a perspective view of an analysis unit as taken out from the housing of the chromatograph shown in FIG. 1;

FIG. 3 is a longitudinal section taken along line II — II in FIG. 1;

Figure 4:
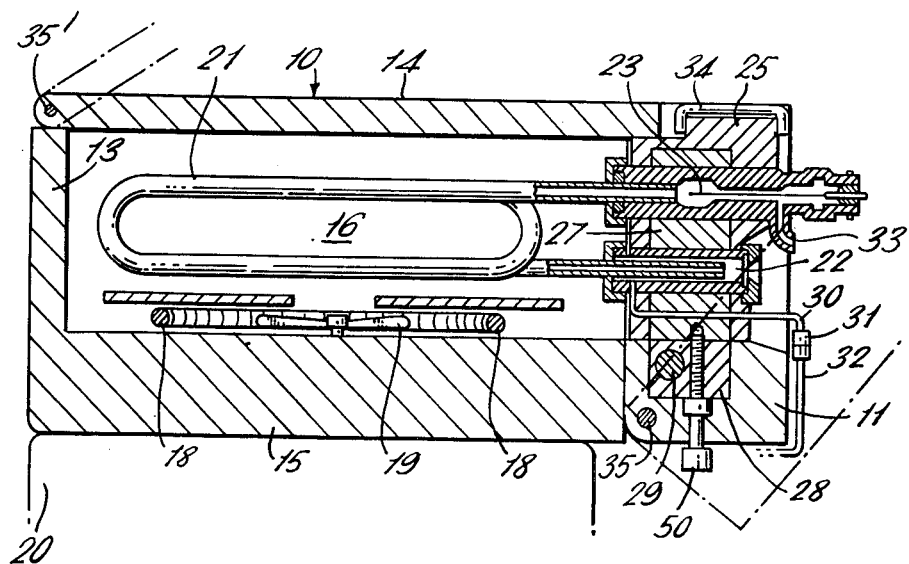
FIG. 4 is a view similar to FIG. 3 but showing another embodiment of the invention.

Referring to the drawings, first to FIGS. 1 to 3, there is shown a chromatograph which comprises a main or principal portion and a subsidiary portion, with the principal portion placed on top the subsidiary portion. The principal portion comprises a housing 10 having a front wall 11, both side walls 12, a rear wall 13, a top wall 14 and a bottom wall 15, which define a column chamber 16 therein. A recess or opening 17 is formed in the front wall of the housing for purposes to be described hereinafter. Inside the housing an electric heater 18 energized by a suitable source (not shown) through a controller 51 is provided on the bottom surface of the housing, with an electric fan 19 for rendering uniform the temperature inside the chamber 16. The walls of the housing are filled with a suitable adiabatic material.

The subsidiary portion includes the temperature controller 51, an indicator and/or recorder, a carrier gas flow rate controller, pumps, etc. Most of these elements are not shown but enclosed in a housing 20.

It is a particular feature of the invention that a column 21, a sample introducing portion 22 and a detector 23 are combined or grouped into what we call an analysis unit or module 24, and that the unit is mounted on the housing 10 in such a manner that it can be easily and housing detached from the housing. In one case a single analysis unit may suffice while in another a plurality of analysis units are required, and there are different ways of so mounting the unit or units on the housing. In the illustrated embodiment there are provided a plurality of analysis units complementarily and detachably fitted into the opening 17 of the housing front wall 11 of the apparatus. The sample introducing portion 22 and the detector 23 are enclosed in a support block 25 made of a suitable adiabatic material, with the column 21 being connected between the device 22 and the detector 23 so as to project from the block 25 to extend inside the chamber 16 when the unit 24 is fitted in place in the front wall opening 17.

In the illustrated embodiment, the opening 17 is so dimensioned as to receive four analysis units arranged side by side to complete the front wall 11. A dummy block 26 of the same direction as the block 25 may replace the analysis unit 24 in the opening 17.

The block 25 encloses a smaller inner block 27 of a thermally conductive material, which in turn substantially encloses the sample introducing portion 22 and the detector 23. The bottom surface of the inner block 27 is exposed at the bottom surface of the block 25. A heating block 28 enclosing an electric heater 29 therein is embedded in the bottom surface of the opening 17, so that when the adiabatic block 25 is placed in the opening, the bottom surface of the metal block 27 contacts the upper surface of the heating block 28 for transfer of heat from the latter to the former and therethrough to the sample introducing portion 22 and the detector 23.

The temperature of the heater 29 is controlled by a suitable controller 52, which can be operated independently of the previously mentioned controller 51, so that each of the two heaters 18 and 29 can advantageously be controlled independently of the other. In the illustrated embodiment all the analysis units provided are heated by the single heating block 28, so that it is unnecessary to provide each analysis unit with an individual heater, with resulting simplification of the structure of the unit and reduction of the cost involved. The single common heating block 28 can be replaced by a plurality of heating blocks individually controlled and so disposed as to be contacted by the analysis units when the latter are placed in the front wall opening 17. With this arrangement, it is possible to control the temperature of each analysis unit separately from the others.

Each analysis unit 24 or the dummy block 26 is secured in place in the front wall opening 17 by means of a screw 50 inserted through the bottom wall 15 and the heating block 28 and then screwed into the metal block 27 as shown in FIG. 3.

The unit 24 has an inlet pipe 30 which communicates at one end with the sample introducing portion 22 and is connectable at the other through a nut 31 to a supply pipe 32 leading to a suitable source of carrier fluid not shown but enclosed in the housing 20 of the subsidiary portion for introduction of the carrier fluid into the unit. There can be provided more than one inlet pipes for introduction of different kinds of carrier gases into the column. The unit 24 also has an outlet conduit 33 connected to the effluent side of the detector for evacuation of the carrier gas. The block 25 is advantageously provided with a handle 34 to facilitate handling of the analysis unit.

The dummy block 26 may be provided with various elements or devices such as a back-flushing passage, with a precut valve inserted therein, a refining passage with an aging valve inserted herein, or a sampling passage with a glass sampling valve inserted therein. The dummy block may include no such passage and/or element at all.

FIG. 4 shows a modified form of the apparatus shown in FIGS. 1 to 3. The embodiment of FIG. 4 is basically the same as the previous embodiment, except that in FIG. 4 the housing front wall 11 is hinged as at 35 or otherwise connected at its lower edge to the bottom wall of the housing so that the front wall with the analysis units thereon can be pulled open about the hinge as shown in dashed lines in FIG. 4. and that the top wall 14 of the housing is also hinged or otherwise connected at its rear side as at 35' to the rear wall 13 of the housing so that the top wall 14 can be lifted open. The arrangement makes it easier to remove the column 21 from the block 25, if required, without removing the unit 24 from the housing front wall 11. Also, by opening the top wall 14 and also the front wall 11, if necessary, it is easily possible to lower the temperature of the column chamber 16 more quickly than otherwise.

Figure 5:
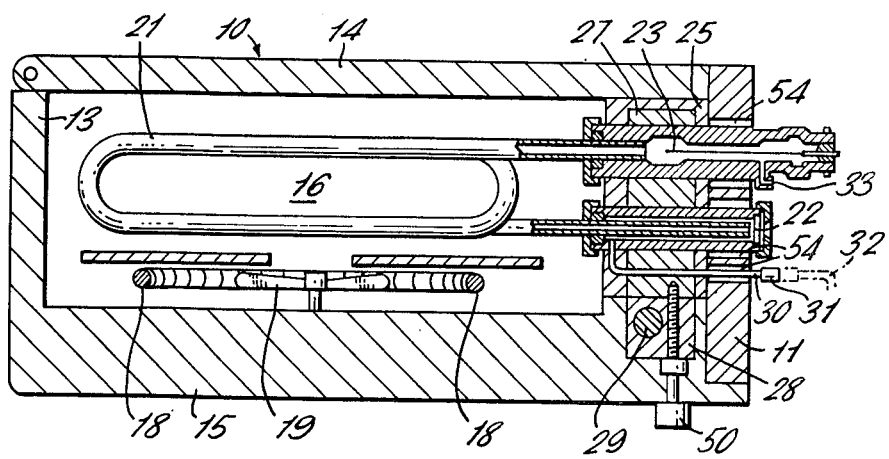
FIG. 5 is a view similar to FIG. 3 but showing a third embodiment of the invention.

FIG. 5 shows a third embodiment of the invention, in which the analysis unit or units are placed just inside the front wall 11, which is hinged or otherwise detachably connected to the housing. The unit 24 carries thereon a sample introducing portion 22 and a detector 23 and a column 21 connected therebetween. The front wall 11 has apertures 54 through which the outer ends of the detector 23, the inlet and outlet pipes 30 and 33 and the sample introducing portion 22 project, or access thereto may be made. The top wall 14 may also conveniently be arranged so as to be lifted open as in the embodiment of FIG. 4. In some application the adiabatic cover or block 25 may be eliminated to expose the metal block 27 to the temperature inside the column chamber 16. In this case the heating block 28 with its heater 29 may also be eliminated.

Figure 6:
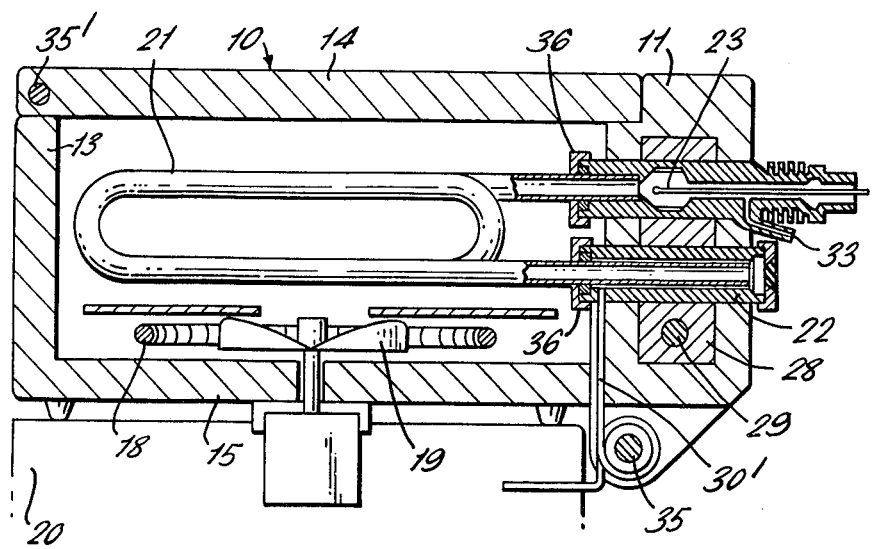
FIG. 6 is a view similar to FIG. 3 but showing a fourth embodiment of the invention.
Figure 7:
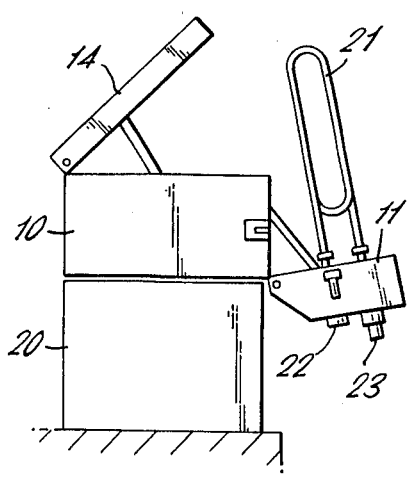
FIG. 7 is a side view showing the embodiment of FIG. 6 with the top and front walls being open.

FIGS. 6 and 7 show a fourth embodiment of the invention, wherein the detachable analysis units in the previous embodiments are not used. The front wall 11 of the housing is hinged as at 35 just as in the case of the previous embodiment of FIG. 4. The housing front wall 11, however, has no such opening as the opening 17 for receiving the blocks 25 in FIGS. 1 to 3, but directly supports the sample introducing portion 22 and the detector 23, with the column 21 being connected between them by a nut 36. The thermally conductive block 28 with the heater 29 therein is enclosed in the adiabatic material of the front wall 11. A supply tube 30' of a flexible material connects the sample introducing portion 22 directly to a source of carrier gas not shown but provided in the subsidiary portion of the apparatus.

In the apparatus shown in FIGS. 6 and 7, when the column 21 is to be removed from the housing for cleaning or replacement, the top wall or lid 14 is lifted open and the front wall 11 pulled forwardly to lie open as shown in FIG. 7, so that the column stands upwardly inclined for quick and easy removal of the column from the front wall 11.

Figure 8:
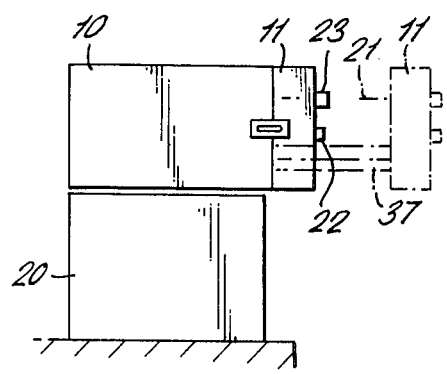
FIG. 8 is a side view of a fifth embodiment of the invention.

A modified form of FIG. 6 is shown in FIG. 8, wherein the front wall 11 of the housing with its column, detector and sample introducing portion can be pulled forwardly on a guide rail 37 just as if it were a drawer. In this case there is no need to arrange so that the top wall 14 of the housing can be lifted like a lid.

The invention has various advantages such as follows:

1. Since the analysis unit is individually detachable from the column chamber or housing, replacement of the column can be effected very easily and speedily. If there are provided many analysis units having different types of columns and/or detectors, mere replacement of the units makes it possible to use a single chromatograph for analysis of a wide variety of samples.

2. It is possible to manufacture the subsidiary portion of the apparatus and the column chambers or housings separately and independently of the analysis units, which latter can be manufactured as demand therefor occurs. This results in rationalization of the manufacturing process and reduction of the cost involved. If the user or customer makes a claim with respect to the analysis units, or the specification of the units has been changed, replacement of the units alone suffices, with resulting reduction of the cost and improvements in services rendered to the customer.

3. Since the analysis units can be easily removed from the housing, or the front wall thereof with the column can be opened to bring the column substantially outside the housing, it is quite easy to exchange the units or remove the column from the housing for cleaning or replacement.

4. The arrangement in known chromatographs of the type is such that the column is attached to a fixed member or wall of the column chamber. Therefore, for removal of the column therefrom it is necessary to move the column horizontally inside the chamber so as to pull its distal ends out of the mounting member. This means that there must be an extra space in the chamber to permit the horizontal movement of the column inside the chamber, with a resulting increase in the size of the chamber. In accordance with this invention, however, since the front wall of the housing or the analysis unit carrying the column can be moved relative to the housing, no such extra space is required of the chamber, so that the housing can be of a compact size.

5. Since the metal block 27 encircling the detector 23 and the sample introducing portion 22 is so arranged as to be brought into contact with the heating block 28 when the analysis unit is placed in the wall opening 17, the temperature of the detector and the sample introducing portion can be simply and easily controlled independently of the temperature control of the column chamber.

6. Since each analysis unit carries the detector and the sample introducing portion encircled by the metal block 27 which is heated by the separate heating block 28, it is not necessary to provide each analysis unit with an individual heater, but the common heating block 28 suffices, so that the structure of the unit becomes the more simple and the cost involved, the lower.

7. Since the outer ends of the sample introducing portion, the detector and the inlet and outlet pipes of the carrier fluid are provided on one and the same surface of the analysis unit, access thereto can easily be made so that operation associated with these elements can be easily and quickly conducted.

What we claim is:

1. A chromatograph comprising a housing having walls defining a column chamber; a plurality of blocks constituting at least a portion of said housing walls so that said blocks are selectively detachable from said housing wall portion, at least one of said blocks carrying thereon a sample introducing portion, a column and a detector so as to form an analysis unit and including an inner block of thermally conductive material enclosing substantial portions of said sample introducing portion and said detector means; means for supplying a carrier fluid to said sample introducing portion; and means for heating said inner block, said heating means contained in said housing and having an exposed surface, said exposed surface adapted to contact a corresponding exposed surface of said inner block of thermally conductive material whereby heat is transferred from said heating means to said inner block when said blocks are attached to said housing.

2. The chromatograph of claim 1, wherein one of said housing walls has an opening formed therein and said plurality of blocks are complementarily fitted into said opening so that said blocks can be individually removed therefrom.

3. The chromatograph of claim 1, wherein said one wall and another of said walls adjacent to said one wall are movable relative to said housing.

4. The chromatopgraph of claim 1, wherein another of said walls adjacent to said wall portion wherein said blocks are fitted is movable relative to said housing.

5. The chromatograph of claim 1, wherein the outer ends of said sample introducing portion and detector are provided at one and the same side of said block so that access thereto can easily be made from outside said housing.

6. The chromatograph of claim 1 wherein there are a plurality of analysis units having different kinds of columns.

7. The chromatograph of claim 1, wherein there are a plurality of analysis units having different kinds of detectors.

8. The chromatograph of claim 1, wherein at least another of said blocks is a dummy block of the same shape and dimension as the block of said analysis unit.

9. The chromatograph of claim 8, wherein said analysis units include different kinds of detectors.

* * * * *